(12) United States Patent
Sugiyama et al.

(10) Patent No.: US 7,498,352 B2
(45) Date of Patent: Mar. 3, 2009

(54) TGF-β SUPERFAMILY PRODUCTION/SECRETION PROMOTER

(75) Inventors: Yasuo Sugiyama, Kawanishi (JP); Masatoshi Hazama, Ikeda (JP); Asae Shintani, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 583 days.

(21) Appl. No.: 10/480,849

(22) PCT Filed: Jun. 25, 2002

(86) PCT No.: PCT/JP02/06350

§ 371 (c)(1),
(2), (4) Date: Dec. 16, 2003

(87) PCT Pub. No.: WO03/000257

PCT Pub. Date: Jan. 3, 2003

(65) Prior Publication Data

US 2004/0142988 A1   Jul. 22, 2004

(30) Foreign Application Priority Data

Jun. 26, 2001   (JP) .............................. 2001-193728

(51) Int. Cl.
*A61K 31/42* (2006.01)
*C07D 263/30* (2006.01)

(52) U.S. Cl. ..................... 514/377; 548/233

(58) Field of Classification Search ................. 514/377; 548/233
See application file for complete search history.

(56) References Cited

U.S. PATENT DOCUMENTS 7,183,276 B2 * 2/2007 Sakai et al. .............. 514/228.2

FOREIGN PATENT DOCUMENTS

| WO | WO99/15191 | 1/1991 |
|---|---|---|
| WO | WO97/03188 | 1/1997 |
| WO | WO98/50060 | 11/1998 |
| WO | WO 01/14372 | 3/2001 |

OTHER PUBLICATIONS

Naschitz et al., Dysautonomia in Chronic fatigue Syndrome: facts, hypotheses, implications, Medical Hypotheses, vol. 62, Issue 2, pp. 203-206, (2004).*

Vizzard, M.A., "Changes in Urinary Bladder Neurotrophic Factor mRNA and NGF Protein Following Urinary Bladder Dysfunction," Experimental Neurology 2000, U.S., vol. 161, No. 1, 2000, pp. 273-284.

Nosrat, C.A., "Neurotrophic Factors in the Tongue: Expression Patterns, Biological Activity, Relation to Innervation and Studies of Neurotrophin Knockout Mice," Annuals of the New York Academy of Science Nov. 30, 1998, vol. 855, Nov. 30, 1998, pp. 28-49.

* cited by examiner

*Primary Examiner*—James Wilson
*Assistant Examiner*—Ebenezer Sackey
(74) *Attorney, Agent, or Firm*—David A. Conlin; Jeffrey L. Kopacz; Edwards Angell Palmer & Dodge LLP

(57) ABSTRACT

The present invention provides a TGF-β superfamily production/secretion promoter comprising a compound represented by the formula

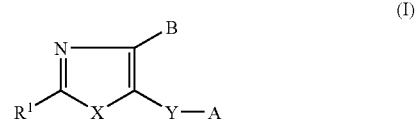

wherein $R^1$ is a halogen atom, an optionally substituted heterocyclic group, an optionally substituted hydroxy group, an optionally substituted thiol group or an optionally substituted amino group; A is an optionally substituted acyl group, an optionally substituted heterocyclic group, an optionally substituted hydroxy group or an optionally esterified or amidated carboxyl group; B is an optionally substituted aromatic group; X is an oxygen atom, a sulfur atom or an optionally substituted nitrogen atom; and Y is a divalent hydrocarbon group or heterocyclic group, or a salt thereof or a prodrug thereof, which is useful as an agent for the prophylaxis or treatment of dysautonomia, bladder dysfunction, hearing impairment, bone disease and the like.

16 Claims, No Drawings

SEQUENCE LISTING

<160> NUMBER OF SEQ ID NOS: 3

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
actgcatgcc aaccagagc                                            19

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
tcgcacctct ggactgagta tc                                        22

<210> SEQ ID NO 3
<211> LENGTH: 25
<212> TYPE: DNA
<213> ORGANISM: Artificial
<220> FEATURE:
<223> OTHER INFORMATION: primer

<400> SEQUENCE: 3
actcagaacc aacccctgac ccagc                                     25

TGF-β SUPERFAMILY PRODUCTION/SECRETION PROMOTER

This application is the National Phase filing of International Patent Application No. PCT/JP02/06350, filed Jun. 25, 2002.

TECHNICAL FIELD

The present invention relates to a TGF-β superfamily production/secretion promoter useful as an agent for the prophylaxis or treatment of dysautonomia, bladder dysfunction, hearing impairment, bone disease and the like.

The present invention also relates to an agent for neuroneogenesis, an agent for restoring nerve function, an agent for the prophylaxis or treatment of dysautonomia and an agent for the prophylaxis or treatment of bladder dysfunction.

BACKGROUND ART

The TGF-β superfamily refers to a protein group that preserves the characteristic arrangement of cysteine in mature molecule, and is known to exhibit diverse actions on various cells and tissues. Particularly, it has a significant effect on the functions of autonomic nerve responsible for various reflexes, various sensory and motor nerves, monoaminergic nerve, cholinergic nerve, GABAergic nerve, glutamatergic nerve and various peptidergic nerves.

Of the TGF-β superfamily, GDNF (glial cell line-derived neurotrophic factor) and GDF (growth/differentiation factor)—15 are known to play an important role for autonomic nerve function responsible for various reflexes, various sensory and motor nerve functions, and monoaminergic nerve function [*Neuron*, 15, p. 1465-1473, 1995; *Nature*, 403, p. 312-316, 2000; *Nature*, 407, p. 1011-1015, 2000; *Journal of Neuroscience*, 20, p. 8597-8603, 2000; *Neuroreport*, 9, p. 2183-2187, 1998].

In the meantime, a compound represented by the formula (I), which is the active ingredient in the present invention, is described in WO01/14372 as a neurotrophin production/secretion promoter.

However, there is no report on the use of said compound as a TGF-β superfamily production/secretion promoter.

DISCLOSURE OF THE INVENTION

An object of the present invention is to provide a TGF-β superfamily production/secretion promoter useful as an agent for the prophylaxis or treatment of dysautonomia, bladder dysfunction, hearing impairment, bone disease and the like.

Another object of the present invention is to provide an agent for neuroneogenesis, an agent for restoring nerve function, an agent for the prophylaxis or treatment of dysautonomia and an agent for the prophylaxis or treatment of bladder dysfunction.

The present inventors have studied in search of a TGF-β superfamily production/secretion promoter and found that a compound represented by the formula

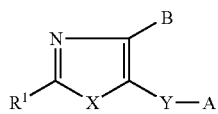

(I)

wherein $R^1$ is a halogen atom, an optionally substituted heterocyclic group, an optionally substituted hydroxy group, an optionally substituted thiol group or an optionally substituted amino group; A is an optionally substituted acyl group, an optionally substituted heterocyclic group, an optionally substituted hydroxy group or an optionally esterified or amidated carboxyl group; B is an optionally substituted aromatic group; X is an oxygen atom, a sulfur atom or an optionally substituted nitrogen atom; and Y is a divalent hydrocarbon group or heterocyclic group, unexpectedly has a superior TGF-β superfamily production/secretion promoting action, which resulted in the completion of the present invention.

Accordingly, the present invention relates to 1) a TGF-β superfamily production/secretion promoter comprising a compound represented by the formula (I), a salt thereof or a prodrug thereof;
2) the agent of the aforementioned 1), wherein $R^1$ is an optionally substituted heterocyclic group;
3) the agent of the aforementioned 1), wherein $R^1$ is an optionally substituted 5-membered nitrogen-containing aromatic heterocyclic group;
4) the agent of the aforementioned 1), wherein $R^1$ is an optionally substituted imidazolyl group;
5) the agent of the aforementioned 1), wherein A is an optionally substituted hydroxy group;
6) the agent of the aforementioned 1), wherein A is an optionally substituted aryloxy group;
7) the agent of the aforementioned 1), wherein A is a phenoxy group substituted by an optionally substituted alkyl group;
8) the agent of the aforementioned 1), wherein B is an optionally substituted phenyl group;
9) the agent of the aforementioned 1), wherein X is an oxygen atom;
10) the agent of the aforementioned 1), wherein Y is a divalent aliphatic hydrocarbon group;
11) the agent of the aforementioned 1), wherein the compound is 4-(4-chlorophenyl)-2-(2-methyl-1-imidazolyl)-5-[3-(2-methylphenoxy)propyl]oxazole;
12) the agent of the aforementioned 1), wherein the TGF-β superfamily is GDNF;
13) the agent of the aforementioned 1), wherein the TGF-β superfamily is GDF-15;
14) the agent of the aforementioned 1), which is an agent for the prophylaxis or treatment of dysautonomia;
15) the agent of the aforementioned 1), which is an agent for the prophylaxis or treatment of bladder dysfunction;
16) an agent for neuroneogenesis comprising a compound represented by the formula (I), a salt thereof or a prodrug thereof;
17) an agent for restoring nerve function, which comprises a TGF-β superfamily production/secretion promoter;
18) an agent for the prophylaxis or treatment of dysautonomia, which comprises a TGF-β superfamily production/secretion promoter;
19) an agent for the prophylaxis or treatment of bladder dysfunction, which comprises a TGF-β superfamily production/secretion promoter;
20) a method for promoting the production and/or secretion of the TGF-β superfamily in a mammal, which comprises administering a compound represented by the formula (I), a salt thereof or a prodrug thereof to the mammal;
21) a method for neuroneogenesis in a mammal, which comprises administering a compound represented by the formula (I), a salt thereof or a prodrug thereof to the mammal;
22) a method for restoring nerve function in a mammal, which comprises administering a TGF-β superfamily production/secretion promoter to the mammal;

23) a method for preventing and/or treating dysautonomia in a mammal, which comprises administering a TGF-β superfamily production/secretion promoter to the mammal;
24) a method for preventing and/or treating bladder dysfunction in a mammal, which comprises administering a TGF-β superfamily production/secretion promoter to the mammal;
25) use of a compound represented by the formula (I), a salt thereof or a prodrug thereof for the production of a TGF-β superfamily production/secretion promoter;
26) use of a compound represented by the formula (I), a salt thereof or a prodrug thereof for the production of an agent for neuroneogenesis;
27) use of a TGF-β superfamily production/secretion promoter for the production of an agent for restoring nerve function;
28) use of a TGF-β superfamily production/secretion promoter for the production of an agent for the prophylaxis or treatment of dysautonomia;
29) use of a TGF-β superfamily production/secretion promoter for the production of an agent for the prophylaxis or treatment of bladder dysfunction; and the like.

In the formula (I), as the heterocyclic group of the "optionally substituted heterocyclic group" for $R^1$ or A, a 5- or 6-membered ring containing 1 to 4 atoms selected from a nitrogen atom, an oxygen atom and a sulfur atom as ring-constituting atoms in addition to carbon atoms, and a condensed ring derived therefrom can be mentioned. As the condensed ring, for example, condensed rings comprising such a 5- or 6-membered ring and a 6-membered ring containing 1 or 2 nitrogen atoms, a benzene ring, or a 5-membered ring containing one sulfur atom can be mentioned.

Specific examples of the heterocyclic group include aromatic heterocyclic groups such as pyridyl (e.g., 2-pyridyl, 3-pyridyl, 4-pyridyl etc.), pyrimidinyl (e.g., 2-pyrimidinyl, 5-pyrimidinyl, 6-pyrimidinyl etc.), pyridazinyl (e.g., 3-pyridazinyl, 4-pyridazinyl etc.), pyrazinyl (e.g., 2-pyrazinyl etc.), pyrrolyl (e.g., 1-pyrrolyl, 2-pyrrolyl etc.), imidazolyl (e.g., 1-imidazolyl, 2-imidazolyl, 4-imidazolyl, 5-imidazolyl etc.), pyrazolyl (e.g., 1-pyrazolyl, 3-pyrazolyl, 4-pyrazolyl etc.), isoxazolyl, isothiazolyl, thiazolyl (e.g., 2-thiazolyl, 4-thiazolyl, 5-thiazolyl etc.), oxazolyl (e.g., 2-oxazolyl, 4-oxazolyl, 5-oxazolyl etc.), 1,2,4-oxadiazolyl (e.g., 1,2,4-oxadiazol-5-yl etc.), 1,2,4-triazolyl (e.g., 1,2,4-triazol-1-yl, 1,2,4-triazol-3-yl etc.), 1,2,3-triazolyl (e.g., 1,2,3-triazol-2-yl, 1,2,3-triazol-4-yl etc.), tetrazolyl (e.g., tetrazol-1-yl, tetrazol-5-yl etc.), benzimidazoyl (e.g., benzimidazol-1-yl, benzimidazol-2-yl etc.), indolyl (e.g., indol-1-yl, indol-3-yl etc.), 1H-indazolyl (e.g., 1H-indazol-1-yl etc.), 1H-pyrrolo[2,3-b]pyrazinyl (e.g., 1H-pyrrolo[2,3-b]pyrazin-1-yl etc.), 1H-pyrrolo[2,3-b]pyridyl (e.g., 1H-pyrrolo[2,3-b]pyridin-1-yl etc.), 1H-imidazo[4,5-b]pyridyl (e.g., 1H-imidazo[4,5-b]pyridin-1-yl etc.), 1H-imidazo[4,5-c]pyridyl (e.g., 1H-imidazo[4,5-c]pyridin-1-yl etc.), 1H-imidazo[4,5-b]pyrazinyl (e.g., 1H-imidazo[4,5-b]pyrazin-1-yl etc.), benzotriazolyl, etc.; and non-aromatic heterocyclic groups such as pyrrolidinyl (e.g., 1-pyrrolidinyl etc.), piperidyl (e.g., 1-piperidyl etc.), morpholinyl (e.g., morpholin-4-yl etc.), thiomorpholinyl (e.g., thiomorpholin-4-yl etc.), piperazinyl (e.g., 1-piperazinyl etc.), hexamethyleniminyl (e.g., hexamethylenimin-1-yl etc.), oxazolidinyl (e.g., oxazolidin-3-yl etc.), thiazolidinyl (e.g., thiazolidin-3-yl, thiazolidin-2-yl etc.), imidazolidinyl (e.g., imidazolidin-3-yl etc.), imidazolinyl (e.g., imidazolin-1-yl, imidazolin-2-yl etc.), oxazolinyl (e.g., oxazolin-2-yl etc.), thiazolinyl (e.g., thiazolin-2-yl etc.), oxazinyl (e.g., oxazin-2-yl etc.), etc. Of these azolyl groups (e.g., pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl), azolinyl groups (e.g., imidazolinyl, oxazolinyl, thiazolinyl), azolidinyl groups (e.g., pyrrolidinyl, oxazolidinyl, thiazolidinyl, imidazolidinyl), and the like are preferable.

The heterocyclic group for $R^1$ or A may have 1 to 3 substituents at substitutable positions. Examples of such substituents include an oxo group, an aliphatic hydrocarbon group, an alicyclic hydrocarbon group, an aryl group, an aromatic heterocyclic group, a non-aromatic heterocyclic group, a halogen atom, a nitro group, an optionally substituted amino group, an optionally substituted acyl group, an optionally substituted hydroxy group, an optionally substituted thiol group, an optionally esterified or amidated carboxy group, and the like.

As the oxo-substituted heterocyclic group, for example, azolidinyl groups substituted by one or two oxo groups and the like can be mentioned. Typical examples thereof include 2-oxoimidazolidinyl (e.g., 2-oxoimidazolidin-1-yl etc.), 2,4-dioxoimidazolidinyl (e.g., 2,4-dioxoimidazolidin-3-yl etc.), 2,4-dioxooxazoldinyl (e.g., 2,4-dioxooxazolidin-3-yl etc.) and 2,4-dioxothiazolidinyl (e.g., 2,4-dioxothiazolidin-3-yl etc.), and the like.

As said aliphatic hydrocarbon group, straight-chain or branched aliphatic hydrocarbon groups containing 1 to 15 carbon atoms, such as alkyl groups, alkenyl groups, alkynyl groups and the like can be mentioned.

Preferable examples of the alkyl groups include alkyl groups containing 1 to 10 carbon atoms, such as methyl, ethyl, propyl, isopropyl, butyl, isobutyl, sec.-butyl, t.-butyl, pentyl, isopentyl, neopentyl, t.-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Preferable examples of the alkenyl groups include alkenyl groups containing 2 to 10 carbon atoms, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferable examples of the alkynyl groups include alkynyl groups containing 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

As said alicyclic hydrocarbon group, saturated or unsaturated alicyclic hydrocarbon groups containing 3 to 12 carbon atoms, such as cycloalkyl groups, cycloalkenyl groups, cycloalkadienyl groups and the like can be mentioned.

Preferable examples of the cycloalkyl groups include cycloalkyl groups containing 3 to 10 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferable examples of the cycloalkenyl groups include cycloalkenyl groups containing 3 to 10 carbon atoms, such as 2-cyclopenten-1-yl, 3-cyclopenten-1-yl, 2-cyclohexen-1-yl, 3-cyclohexen-1-yl and the like.

Preferable examples of the cycloalkadienyl groups include cycloalkadienyl groups containing 4 to 10 carbon atoms, such as 2,4-cyclopentadien-1-yl, 2,4-cyclohexadien-1-yl, 2,5-cyclohexadien-1-yl and the like.

The aryl group means a monocyclic or condensed polycyclic aromatic hydrocarbon group, and preferable examples thereof include aryl groups containing 6 to 14 carbon atoms, such as phenyl, naphthyl, anthryl, phenanthryl, acenaphthylenyl and the like. Of these, preferred are phenyl, 1-naphthyl, 2-naphthyl and the like.

Preferable examples of the aromatic heterocyclic group include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.; aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl etc.; and the like.

Preferable examples of the non-aromatic heterocyclic group include oxiranyl, azetidinyl, oxetanyl, thietanyl, tetrahydrofuryl, thiolanyl, piperidyl, tetrahydropyranyl, morpholinyl, thiomorpholinyl, piperazinyl, pyrrolidinyl and the like.

Examples of the halogen atom include fluorine, chlorine, bromine and iodine. Particularly preferred are fluorine and chlorine.

Examples of the optionally substituted amino group include an amino group (—NH$_2$ group) which may be mono- or di-substituted by a substituent selected from alkyl groups containing 1 to 10 carbon atoms, which may be substituted by hydroxy, alkenyl groups containing 2 to 10 carbon atoms, cycloalkyl groups containing 3 to 10 carbon atoms, acyl groups containing 1 to 10 carbon atoms (e.g., formyl, $C_{1-9}$ alkyl-carbonyl etc.), aromatic groups containing 6 to 12 carbon atoms (e.g., $C_{6-12}$ aryl groups such as phenyl etc. and the like) and aralkyl groups containing 7 to 10 carbon atoms (e.g., benzyl etc.). Examples of the substituted amino group include methylamino, dimethylamino, ethylamino, diethylamino, dibutylamino, diallylamino, cyclohexylamino, acetylamino, propionylamino, benzoylamino, phenylamino, N-methyl-N-phenylamino, N-methyl-N-benzylamino, N-methyl-N-hydroxyethylamino and the like.

Examples of the acyl group of the optionally substituted acyl groups include acyl groups containing 1 to 13 carbon atoms, specifically formyl and, for example, groups resulting from binding of an alkyl group containing 1 to 10 carbon atoms, a cycloalkyl group containing 3 to 10 carbon atoms, an alkenyl group containing 2 to 10 carbon atoms, a cycloalkenyl group containing 3 to 10 carbon atoms or an aromatic group containing 6 to 12 carbon atoms (e.g., $C_{6-12}$ aryl group such as phenyl etc. and the like) to a carbonyl group (e.g., $C_{1-10}$ alkyl-carbonyl groups such as acetyl, propionyl, butyryl, isobutyryl, valeryl, isovaleryl, pivaloyl, hexanoyl, heptanoyl, octanoyl etc.; $C_{3-10}$ cycloalkyl-carbonyl groups such as cyclobutanecarbonyl, cyclopentanecarbonyl, cyclohexanecarbonyl, cycloheptanecarbonyl etc.; $C_{2-10}$ alkenylcarbonyl groups such as crotonyl etc.; $C_{3-10}$ cycloalkenylcarbonyl groups such as 2-cyclohexenecarbonyl etc.; and $C_{6-12}$ aryl-carbonyl groups such as benzoyl, nicotinoyl etc.); a phosphono group, and the like. Examples of the substituent of the substituted acyl groups include alkyl groups containing 1 to 3 carbon atoms, alkoxy groups containing 1 to 3 carbon atoms, halogen atoms (e.g., chlorine, fluorine, bromine etc.), a nitro group, a hydroxyl group, an amino group and the like.

Referring to the optionally substituted hydroxy group, examples of the substituted hydroxy group include alkoxy groups which may be substituted by optionally halogenated $C_{1-6}$ alkyl-carbonylamino (e.g., trifluoroacetylamino etc.); alkenyloxy groups; cycloalkyloxy groups; cycloalkenyloxy groups; aralkyloxy groups; acyloxy groups; optionally substituted aryloxy groups; alkylsulfonyloxy groups; arylsulfonyloxy group which may be substituted by a $C_{1-6}$ alkyl group (e.g., methyl etc.); an indanyloxy group; and a tetrahydronaphthoxy group which may be substituted by 1 to 4 $C_{1-6}$ alkyl (e.g., methyl etc.).

Preferable examples of the alkoxy groups include alkoxy groups containing 1 to 10 carbon atoms, such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy and the like.

Preferable examples of the alkenyloxy groups include alkenyloxy groups containing 2 to 10 carbon atoms, such as allyloxy, crotyloxy, 2-pentenyloxy, 3-hexenyloxy and the like.

Preferable examples of the cycloalkyloxy groups include cycloalkyloxy groups containing 3 to 7 carbon atoms, such as cyclobutoxy, cyclopentyloxy, cyclohexyloxy and the like.

Preferable examples of the cycloalkenyloxy groups include cycloalkenyloxy groups containing 5 to 7 carbon atoms, such as 2-cyclopentenyloxy, 2-cyclohexenyloxy and the like.

Preferable examples of the aralkyloxy groups include aralkyloxy groups containing 7 to 10 carbon atoms such as phenyl-$C_{1-4}$ alkyloxy groups (e.g., benzyloxy, phenethyloxy etc.), and the like.

Preferable examples of the acyloxy groups include acyloxy groups containing 2 to 13 carbon atoms, more preferably alkanoyloxy groups containing 2 to 4 carbon atoms (e.g., acetyloxy, propionyloxy, butyryloxy, isobutyryloxy etc.), and the like.

Preferable examples of the aryloxy groups of the "optionally substituted aryloxy groups" include aryloxy groups containing 6 to 14 carbon atoms such as phenoxy, naphthyloxy and the like. Said aryloxy groups (preferably a phenoxy group) may have 1 to 3 (preferably 1 or 2) substituents. Examples of such substituents include halogen atoms (e.g., chlorine, fluorine, bromine etc.); optionally halogenated alkoxy groups containing 1 to 4 carbon atoms (e.g., methoxy, ethoxy, propoxy, isopropoxy, trifluoromethoxy etc.); alkyl groups containing 1 to 4 carbon atoms (e.g., methyl, ethyl, propyl, isopropyl, butyl, isobutyl, t.-butyl etc.) which may be substituted by a hydroxy group, a carboxyl group, $C_{1-6}$ alkoxy-carbonyl groups (e.g., methoxycarbonyl etc.) or a cyano group; a cyano group; a carboxyl group; a hydroxy group; $C_{6-14}$ aryloxy groups (e.g., phenoxy etc.); $C_{1-6}$ alkoxy-carbonyl groups (e.g., methoxycarbonyl etc.); $C_{1-6}$ alkylsulfanyl groups (e.g., methylsulfanyl etc.); $C_{1-6}$ alkyl-carbonyloxy groups (e.g., acetyloxy etc.), and the like. As the substituted aryloxy group, for example, 2-, 3- or 4-chlorophenoxy; 2-, 3- or 4-methoxyphenoxy; 2, 3- or 4-methylphenoxy; 2-, 3- or 4-cyanophenoxy; 2-, 3- or 4-hydroxyphenoxy, and the like can be mentioned.

Preferable examples of the alkylsulfonyloxy group include alkylsulfonyloxy groups containing 1 to 10 carbon atoms, such as methylsulfonyloxy, ethylsulfonyloxy and the like.

Preferable examples of the arylsulfonyloxy groups which may be substituted by a $C_{1-6}$ alkyl group (e.g., methyl etc.) include arylsulfonyloxy groups containing 6 to 12 carbon atoms which may be substituted by a $C_{1-6}$ alkyl group (e.g., methyl etc.), such as phenylsulfonyloxy, 4-methylphenylsulfonyloxy and the like.

Referring to the optionally substituted thiol group (optionally substituted mercapto group), examples of the substituted thiol group include alkylsulfanyl groups which may be substituted by a hydroxyl group; cycloalkylsulfanyl groups; arylsulfanyl groups which may be substituted by a $C_{1-6}$ alkyl group (e.g., methyl etc.); heteroarylsulfanyl groups; aralkylsulfanyl groups; heteroarylalkylsulfanyl groups; acylsulfanyl groups; and the like.

Preferable examples of the alkylsulfanyl groups include alkylsulfanyl groups containing 1 to 10 carbon atoms (e.g., methylsulfanyl, ethylsulfanyl, propylsulfanyl, isopropylsulfanyl, butylsulfanyl, isobutylsulfanyl, sec.-butylsulfanyl, t.-butylsulfanyl, pentylsulfanyl, isopentylsulfanyl, neopentylsulfanyl, hexylsulfanyl, heptylsulfanyl, nonylsulfanyl etc.) and the like.

Preferable examples of the cycloalkylsulfanyl groups include cycloalkylsulfanyl groups containing 3 to 7 carbon atoms (e.g., cyclobutylsulfanyl, cyclopentylsulfanyl, cyclohexylsulfanyl etc.), and the like.

Preferable examples of the arylsulfanyl groups which may be substituted by a $C_{1-6}$ alkyl group include arylsulfanyl groups containing 6 to 14 carbon atoms which may be substituted by a $C_{1-6}$ alkyl group, such as phenylsulfanyl, naphthylsulfanyl, 4-methylphenylsulfanyl, and the like.

Examples of the heteroarylsulfanyl groups include a thiol group substituted by the aromatic heterocyclic group mentioned above, and the like. Of these, preferred are 2-pyridylsulfanyl, 3-pyridylsulfanyl, 2-imidazolylsulfanyl, 1,2,4-triazol-5-ylsulfanyl, 2-pyrimidinylsulfanyl, and the like.

Preferable examples of the aralkylsulfanyl groups include aralkylsulfanyl groups containing 7 to 10 carbon atoms, such as phenyl-$C_{1-4}$ alkylsulfanyl groups (e.g., benzylsulfanyl, phenethylsulfanyl etc.), and the like.

Examples of the heteroarylalkylsulfanyl groups include an alkylsulfanyl group substituted by the aromatic heterocyclic groups mentioned above. The alkylsulfanyl group includes, for example, the same alkylsulfanyl groups mentioned above. Preferable examples of the heteroarylalkylsulfanyl group include pyridyl-$C_{1-4}$ alkylsulfanyl groups (e.g., 2-pyridylmethylsulfanyl, 3-pyridylmethylsulfanyl etc.), and the like.

Preferable examples of the acylsulfanyl groups include acylsulfanyl groups containing 2 to 13 carbon atoms, more preferably alkanoylsulfanyl groups containing 2 to 4 carbon atoms (e.g., acetylsulfanyl, propionylsulfanyl, butyrylsulfanyl, isobutyrylsulfanyl etc.), and the like.

Referring to the carboxy group which may be esterified or amidated, examples of the esterified carboxy group include alkoxycarbonyl groups, aralkyloxycarbonyl groups, aryloxycarbonyl groups which may be substituted by a $C_{1-6}$ alkyl group, heteroarylalkyloxycarbonyl groups and the like.

Preferable examples of the alkoxycarbonyl groups include alkoxycarbonyl groups containing 2 to 5 carbon atoms, such as, $C_{1-4}$ alkoxy-carbonyl groups such as methoxycarbonyl, ethoxycarbonyl, propoxycarbonyl, butoxycarbonyl and the like.

Preferable examples of the aralkyloxycarbonyl groups include aralkyloxycarbonyl groups containing 8 to 10 carbon atoms, such as $C_{7-9}$ aralkyloxy-carbonyl groups (e.g., benzyloxycarbonyl etc.), and the like.

Preferable examples of the aryloxycarbonyl groups which may be substituted by a $C_{1-6}$ alkyl group include aryloxycarbonyl groups containing 7 to 15 carbon atoms, which may be substituted by a $C_{1-6}$ alkyl group, such as $C_{6-14}$ aryloxycarbonyl groups (e.g., phenoxycarbonyl, p-tolyloxycarbonyl etc.), and the like.

Examples of the heteroarylalkyloxycarbonyl groups include alkyloxycarbonyl groups substituted by the aromatic heterocyclic group mentioned above. As the alkyloxycarbonyl groups, the same alkoxycarbonyl groups mentioned above can be recited. Preferable examples of the heteroarylalkyloxycarbonyl groups include pyridyl-$C_{1-4}$ alkoxycarbonyl groups (e.g., 2-pyridylmethoxycarbonyl, 3-pyridylmethoxycarbonyl etc.), and the like.

Referring to the carboxyl group which may be esterified or amidated, the amidated carboxyl group includes groups of the formula: —CON($R^5$)($R^6$) wherein $R^5$ and $R^6$ are the same or different and each represents a hydrogen atom, an optionally substituted hydrocarbon group, an optionally substituted hydroxy group or an optionally substituted heterocyclic group, and the like.

Examples of the hydrocarbon group of the optionally substituted hydrocarbon group for $R^5$ or $R^6$ include the aliphatic hydrocarbon group, alicyclic hydrocarbon group, aryl group and the like, which are the exemplified substituents of the heterocyclic group for $R^1$ or A. The optionally substituted hydroxy group for $R^5$ or $R^6$ includes the same as those mentioned above. Further, examples of the heterocyclic group of the optionally substituted heterocyclic group for $R^5$ or $R^6$ include the aromatic heterocyclic groups and the like, which are exemplified as the substituents of the heterocyclic group for $R^1$ or A. As the substituents of the "optionally substituted hydrocarbon group" and "optionally substituted heterocyclic group" for $R^5$ or $R^6$, 1 to 3 substituents selected from halogen atoms (e.g., chlorine, fluorine, bromine, iodine etc.), alkyl groups containing 1 to 4 carbon atoms and alkoxy groups containing 1 to 4 carbon atoms and the like can be mentioned.

Referring to the formula (I), when the substituents on the heterocyclic group for $R^1$ or A are substituents containing an aliphatic hydrocarbon group, an alicyclic hydrocarbon group, an aryl group, an aromatic heterocyclic group, a non-aromatic heterocyclic group etc., they may further have 1 or more, preferably 1 to 3, appropriate substituents. Examples of such substituents include alkyl groups containing 1 to 6 carbon atoms which may be halogenated or substituted by substituents selected from a carboxyl group, an alkoxycarbonyl group containing 2 to 8 carbon atoms, a hydroxy group and an optionally halogenated alkoxy group containing 1 to 4 carbon atoms; alkenyl groups containing 2 to 6 carbon atoms; alkynyl groups containing 2 to 6 carbon atoms; cycloalkyl groups containing 3 to 7 carbon atoms; aryl groups containing 6 to 14 carbon atoms (e.g., phenyl, naphthyl etc.); aromatic heterocyclic groups (e.g., thienyl, furyl, pyridyl, oxazolyl, thiazolyl etc.); non-aromatic heterocyclic groups (e.g., tetrahydrofuryl, morpholinyl, thiomorpholinyl, piperidyl, pyrrolidinyl, piperazinyl etc.); aralkyl groups containing 7 to 9 carbon atoms (e.g., benzyl etc.); an amino group; N-mono($C_{1-4}$) alkylamino groups; N,N-di($C_{1-4}$)alkylamino groups; acylamino groups containing 2 to 8 carbon atoms (e.g., $C_{1-7}$ alkylcarbonylamino such as acetylamino, propionylamino etc.; benzoylamino and the like); an amidino group; acyl groups containing 2 to 8 carbon atoms (e.g., $C_{1-7}$ alkyl-carbonyl such as acetyl etc. and the like); a carbamoyl group; an N-mono($C_{1-4}$)alkylcarbamoyl group; N,N-di($C_{1-4}$)alkylcarbamoyl group; a sulfamoyl group; an N-mono($C_{1-4}$)alkylsulfamoyl group; an N,N-di($C_{1-4}$)alkylsulfamoyl group; a carboxyl group; an alkoxycarbonyl group containing 2 to 8 carbon atoms; a hydroxy group; an optionally halogenated alkoxy group containing 1 to 4 carbon atoms; an alkenyloxy group containing 2 to 5 carbon atoms; a cycloalkyloxy group containing 3 to 7 carbon atoms; an aralkyloxy group containing 7 to 9 carbon atoms (e.g., benzyloxy etc.); an aryloxy group containing 6 to 14 carbon atoms (e.g., phenyloxy, naphthyloxy etc.); a mercapto group; an optionally halogenated alkylsulfanyl group containing 1 to 4 carbon atoms; an aralkylsulfanyl group containing 7 to 9 carbon atoms (e.g., benzylsulfanyl etc.); an arylsulfanyl group containing 6 to 14 carbon atoms (e.g., phenylsulfanyl, naphthylsulfanyl etc.); a sulfo group; a cyano group; an azido group; a nitro group; a nitroso group; and halogen atoms (e.g., fluorine, chlorine, bromine, iodine etc.), and the like.

Referring to the formula (I), the halogen atom, the optionally substituted hydroxy group, the optionally substituted thiol group and the optionally substituted amino group, for $R^1$, respectively include those exemplified as the substituent of the heterocyclic group for $R^1$ or A.

Referring to the formula (I), $R^1$ is preferably an optionally substituted heterocyclic group. $R^1$ is preferably an optionally substituted nitrogen-containing heterocyclic group or an optionally substituted aromatic heterocyclic group. Of these, $R^1$ is preferably an optionally substituted 5-membered nitrogen-containing aromatic heterocyclic group, especially preferably an optionally substituted imidazolyl group.

Referring to the formula (I), the optionally substituted acyl group, the optionally substituted hydroxy group, and the optionally esterified or amidated carboxy group, for A, respectively include those exemplified as the substituent of the heterocyclic group for $R^1$ or A, and the like.

Referring to the formula (I), A is preferably an optionally substituted hydroxy group. Of these, A is preferably an optionally substituted aryloxy group. Particularly preferred is a phenoxy group which may be substituted by an optionally substituted alkyl group (preferably a phenoxy group which may be substituted by an alkyl group). As A, a phenoxy group, which may be substituted by an alkyl group containing 1 to 4 carbon atoms, is especially preferable.

Referring to the formula (I), examples of the aromatic group of the optionally substituted aromatic group for B include an aromatic hydrocarbon group, an aromatic heterocyclic group, and the like.

Preferable examples of the aromatic hydrocarbon group include aromatic hydrocarbon groups containing 6 to 14 carbon atoms, such as aryl groups containing 6 to 14 carbon atoms (e.g., phenyl, naphthyl), and the like.

Preferable examples of the aromatic heterocyclic group include those exemplified as the substituents of the heterocyclic group for $R^1$ or A. Of these, furyl, thienyl, pyridyl, quinolyl, and the like are preferable.

Examples of the substituents on the optionally substituted aromatic group for B include 1 to 3 substituents selected from a halogen atom, a nitro group, a cyano group, an optionally substituted alkoxy group, an optionally substituted alkyl group, an optionally substituted cycloalkyl group and the like.

Examples of the halogen atom include fluorine, chlorine, bromine, iodine, etc.

Examples of the alkoxy group of the optionally substituted alkoxy group include those exemplified as the substituents of the heterocyclic group for $R^1$ or A. Of these, straight-chain or branched alkoxy groups containing 1 to 6 carbon atoms are preferable.

Examples of the alkyl group of the optionally substituted alkyl group include those exemplified as the substituents of the heterocyclic group for $R^1$ or A. Of these, straight-chain or branched alkyl groups containing 1 to 6 carbon atoms are preferable.

Examples of the cycloalkyl group of the optionally substituted cycloalkyl group include those exemplified as the substituents of the heterocyclic group for $R^1$ or A. Of these, cycloalkyl groups containing 3 to 7 carbon atoms are preferable.

Examples of the substituents of the optionally substituted alkoxy group, the optionally substituted alkyl group, and the optionally substituted cycloalkyl group, which are mentioned above, include 1 to 3 substituents selected from halogen atoms (e.g., fluorine, chlorine, bromine, iodine etc.), a hydroxy group and alkoxy groups containing 1 to 6 carbon atoms.

Examples of the substituted alkoxy group include trifluoromethoxy, difluoromethoxy, 2,2,2-trifluoroethoxy, 1,1-difluoroethoxy and the like.

Examples of the substituted alkyl group include trifluoromethyl, difluoromethyl, 2,2,2-trifluoroethyl, trichloromethyl, 1-hydroxymethyl, methoxymethyl, ethoxymethyl, 2-methoxyethyl, 2,2-dimethoxyethyl and the like.

Referring to the formula (I), B is preferably an optionally substituted aromatic hydrocarbon group, and more preferably an optionally substituted phenyl group. For B, a phenyl group which may be substituted by a halogen atom (preferably chlorine) is especially preferable.

Referring to the formula (I), X represents an oxygen atom, a sulfur atom or an optionally substituted nitrogen atom.

As the optionally substituted nitrogen atom for X, —$NR^4$— wherein $R^4$ represents a hydrogen atom, an optionally substituted hydrocarbon group, an optionally substituted acyl group, or an optionally substituted heterocyclic group and the like can be mentioned.

As the optionally substituted hydrocarbon group for $R^4$, those exemplified for $R^5$ mentioned above can be recited.

As the optionally substituted acyl group for $R^4$, those exemplified as the substituents of the heterocyclic group for $R^1$ or A can be recited.

As the optionally substituted heterocyclic group for $R^4$, the same optionally substituted heterocyclic group for $R^1$ or A can be mentioned.

$R^4$ is preferably a hydrogen atom, an optionally substituted hydrocarbon group, and the like. A hydrogen atom and an optionally substituted alkyl group are more preferable. A hydrogen atom, a lower ($C_{1-4}$) alkyl group, and the like are especially preferable.

As X, an oxygen atom and a sulfur atom are preferable, and an oxygen atom is more preferable.

Referring to the formula (I), examples of the divalent hydrocarbon group for Y include a divalent aliphatic hydrocarbon group, a divalent alicyclic hydrocarbon group, and a divalent aromatic hydrocarbon group and the like.

The divalent aliphatic hydrocarbon group for Y may be straight-chain or branched and may be saturated or unsaturated. Said aliphatic hydrocarbon group includes, for example, those divalent groups formed by removing one hydrogen atom from the aliphatic hydrocarbon group exemplified as the substituents of the heterocyclic group for $R^1$ or A, and the like. Of these, those containing 1 to 7 carbon atoms are preferable. As specific examples thereof, for example, saturated ones (e.g., alkylene groups) such as —$CH_2$—, —$CH(CH_3)$—, —$(CH_2)_2$—, —$CH(C_2H_5)$—, —$(CH_2)_3$—, —$(CH_2)_4$—, —$(CH_2)_5$—, —$(CH_2)_6$—, —$(CH_2)_7$— etc.; and unsaturated ones (e.g., alkenylene groups, alkadienylene groups, alkatrienylene groups) such as —CH=CH—, —$C(CH_3)$=CH—, —CH=CH—$CH_2$—, —$C(C_2H_5)$=CH—, —$CH_2$—CH=CH—$CH_2$—, —$CH_2$—$CH_2$—CH=CH—$CH_2$—, —CH=CH—CH=CH—$CH_2$—, —CH=CH—CH=CH—$CH_2$—, etc can be mentioned. The divalent aliphatic hydrogen group for Y is preferably a divalent aliphatic hydrocarbon group containing 1 to 4 carbon atoms, more preferably a saturated one.

The divalent alicyclic hydrocarbon group for Y includes the divalent group formed by removing one hydrogen atom from the alicyclic hydrocarbon group exemplified as the substituents of the heterocyclic group for $R^1$ or A, and the like.

The divalent aromatic hydrocarbon group for Y includes the divalent group formed by removing one hydrogen atom from the aryl groups exemplified as the substituents of the heterocyclic group for $R^1$ or A, and the like.

Referring to the formula (I), examples of the divalent heterocyclic group for Y include a divalent aromatic heterocyclic group, a divalent non-aromatic hydrocarbon group and the like.

The divalent aromatic heterocyclic group for Y includes the divalent group formed by removing one hydrogen atom from the aromatic heterocyclic group exemplified as the substituents of the heterocyclic group for $R^1$ or A, and the like.

The divalent non-aromatic hydrocarbon group for Y includes the divalent group formed by removing one hydrogen atom from the non-aromatic hydrocarbon group exemplified as the substituents of the heterocyclic group for $R^1$ or A.

Referring to the formula (I), Y is preferably a divalent aliphatic hydrocarbon group. An alkylene group (preferably $C_{1-4}$ alkylene group) is more preferable. Preferable concrete examples of Y include —$(CH_2)_3$— and —$(CH_2)_4$—.

As the compound represented by the formula (I) (hereinafter sometimes to be abbreviated as "compound (I)"), the following compounds are preferable.

(1) A compound of the formula (I), wherein $R^1$ is an optionally substituted heterocyclic group, and said heterocyclic group is (i) a 5- or 6-membered ring containing, as ring-constituting atoms in addition to carbon atoms, 1 to 4 atoms selected from a nitrogen atom, an oxygen atom and a sulfur atom, or (ii) a condensed ring of such 5- or 6-membered ring and a 6-membered ring containing 1 or 2 nitrogen atoms, benzene ring or a 5-membered ring containing one nitrogen atom (more preferably an azolyl group).

(2) A compound of the formula (I), wherein A is an optionally substituted hydroxy group, more preferably (i) a hydroxy group, (ii) a $C_{1-10}$ alkoxy group, (iii) a $C_{2-10}$ alkenyloxy group, (iv) a $C_{7-10}$ aralkyloxy group, (v) a $C_{2-13}$ acyloxy group, (vi) a $C_{6-14}$ aryloxy group which may be substituted by 1 to 3 halogen atoms, a $C_{1-6}$ alkyl group or a $C_{1-4}$ alkoxy group, or (vii) a $C_{1-10}$ alkylsulfonyloxy group.

(3) A compound of the formula (I), wherein Y is a divalent aliphatic hydrocarbon group containing 1 to 7 carbon atoms, more preferably a divalent aliphatic hydrocarbon group containing 2 to 4 carbon atoms.

(4) A compound of the formula (I), wherein $R^1$ is (i) a halogen atom, (ii) an imidazolyl, pyrazolyl, 1,2,4-triazolyl, 1,2,3-triazolyl, benzimidazolyl, pyrrolidinyl, piperidinyl, morpholinyl or hexamethyleniminyl group, which may have 1 to 3 substituents selected from a $C_{1-10}$ alkyl group, a $C_{6-14}$ aryl group and a $C_{1-10}$ alkylsulfanyl group, (iii) a $C_{1-10}$ alkoxy group, (iv) a $C_{6-14}$ aryloxy group, (v) a $C_{1-10}$ alkylsulfanyl group, (vi) a $C_{6-14}$ arylsulfanyl group which may be substituted by a $C_{1-6}$ alkyl group, (vii) a thiol group substituted by imidazolyl, 1,2,3-triazolyl, 1,2,4-triazolyl or pyridyl, which may be substituted by a $C_{1-6}$ alkyl group or a $C_{6-14}$ aryl group, (viii) a pyridyl-$C_{1-4}$ alkylsulfanyl group or (ix) an amino group which may be substituted by 1 or 2 of a $C_{1-10}$ alkyl group or a $C_{3-10}$ cycloalkyl group;

A is (i) a formyl group, (ii) imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group, which may be substituted by a $C_{1-10}$ alkyl group, (iii) a hydroxy group, (iv) a $C_{6-14}$ aryloxy group which may be substituted by a halogen atom, a $C_{1-6}$ alkyl group or a $C_{1-4}$ alkoxy group, (v) a $C_{1-10}$ alkylsulfonyloxy group, (vi) a $C_{1-4}$ alkoxy-carbonyl group, (vii) a $C_{7-9}$ aralkyloxy-carbonyl group or (viii) a group of the formula: —$CON(R^5)(R^6)$ wherein $R^5$ and $R^6$ independently represent a hydrogen atom or a $C_{1-10}$ alkyl group which may be substituted by a $C_{1-10}$ alkoxy group or a halogen atom;

B is a phenyl group which may be substituted by a halogen atom; and

Y is —$(CH_2)_2$—, —$(CH_2)_3$—, —$(CH_2)_4$—, —$(CH_2)_5$— or —$(CH_2)_6$—.

(5) A compound of the formula (I), wherein $R^1$ is an optionally substituted heterocyclic group; A is an optionally substituted hydroxy group; and Y is a divalent aliphatic hydrocarbon group containing 1 to 7 carbon atoms.

(6) A compound of the above (5), wherein the heterocyclic group for $R^1$ is an azolyl group (e.g., pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl or tetrazolyl group).

(7) A compound of the above (5), wherein $R^1$ is an azolyl group (e.g., imidazol, pyrazolyl, 1,2,4-triazolyl, 1,2,3-triazolyl etc.) which may have 1 to 3 substituents selected from a $C_{1-10}$ alkyl group, a $C_{6-14}$ aryl group and a $C_{1-10}$ alkylsulfanyl group.

(8) A compound of the above (5), wherein A is (i) a hydroxy group, (ii) a $C_{1-10}$ alkoxy group, (iii) a $C_{2-10}$ alkenyloxy group, (iv) a $C_{7-10}$ aralkyloxy group, (v) a $C_{2-13}$ acyloxy group, (vi) a $C_{6-14}$ aryloxy group which may be substituted by 1 to 3 of a halogen atom, a $C_{1-6}$ alkyl group and a $C_{1-4}$ alkoxy group or (vii) a $C_{1-10}$ alkylsulfonyloxy group, more preferably a $C_{6-14}$ aryloxy group which may be substituted by 1 to 3 of a halogen atom, a $C_{1-6}$ alkyl group and a $C_{1-4}$ alkoxy group.

(9) A compound of the above (5), wherein B is an optionally substituted phenyl group, more preferably a phenyl group which may be substituted by a halogen atom.

(10) A compound of the above (5), wherein Y is a divalent aliphatic hydrocarbon group containing 3 to 5 carbon atoms, more preferably —$(CH_2)_3$—, —$(CH_2)_4$— or —$(CH_2)_5$—.

(11) A compound of the formula (I), wherein

A is an aryloxy group substituted by alkyl, preferably an aryloxy group containing 6 to 14 carbon atoms (preferably phenoxy) substituted by an alkyl group containing 1 to 4 carbon atoms, more preferably a group of the formula:

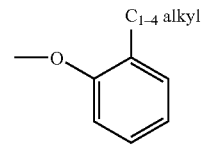

wherein $C_{1-4}$ alkyl is methyl, ethyl, propyl, isopropyl etc., preferably methyl etc.;

$R^1$ is an optionally substituted 5-membered nitrogen-containing aromatic heterocyclic group, preferably an optionally substituted imidazolyl group, more preferably an imidazolyl group which may be substituted by a $C_{1-10}$ alkyl group, especially preferably a group of the formula:

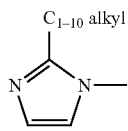

wherein $C_{1-10}$ alkyl is methyl, ethyl, propyl, isopropyl, butyl, pentyl, hexyl etc., preferably $C_{1-4}$ alkyl groups such as methyl, ethyl, propyl, isopropyl, etc., more preferably methyl etc.;

B is an optionally substituted phenyl group, preferably a phenyl group which is optionally substituted by a halogen atom, more preferably a group of the formula:

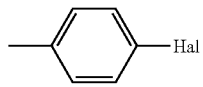

wherein Hal is a halogen atom such as fluorine, chlorine, bromine, iodine etc., preferably chlorine; and Y is a divalent aliphatic hydrocarbon group, preferably a divalent aliphatic hydrocarbon group containing 1 to 4 carbon atoms, more preferably $C_{1-4}$ alkylene groups such as —$CH_2$—, —$(CH_2)_2$—, —$(CH_2)_3$—, —$(CH_2)_4$— etc., especially preferably —$(CH_2)_3$—.

(12) A compound which is 4-(4-chlorophenyl)-2-(2-methyl-1-imidazolyl)-5-oxazolepropanol or a salt thereof, 4-(4-chlorophenyl)-2-(2-methyl-1-imidazolyl)-5-oxazolebutanol or a salt thereof, 4-(4-chlorophenyl)-5-[3-(1-imidazolyl)propyl]-2-(2-methyl-1-imidazolyl)oxazol or a salt thereof, 4-(4-chlorophenyl)-2-(2-methyl-1-imidazolyl)-5-oxazolepentanol or a salt thereof, or 4-(4-chlorophenyl)-5-[4-(1-imidazolyl)butyl]-2-(2-methyl-1-imidazolyl)oxazole or a salt thereof.

Preferable specific examples of the compound represented by the formula (I) include the following compounds (1) to (7):

(1) 4-(4-chlorophenyl)-5-[3-(2-methoxyphenoxy)propyl]-2-(2-methyl-1-imidazolyl)oxazole (2) 3-[3-[4-(4-chlorophenyl)-2-(2-methyl-1-imidazolyl)-5-oxazolyl]propyl]-1-methyl-2,4-imidazolidinedione (3) 4-(4-chlorophenyl)-5-[3-(3-methoxyphenoxy)propyl]-2-(2-methyl-1-imidazolyl)oxazole (4) 4-(4-chlorophenyl)-5-[3-(4-methoxyphenoxy)propyl]-2-(2-methyl-1-imidazolyl)oxazole (5) 4-(4-chlorophenyl)-2-(2-methyl-1-imidazolyl)-5-[3-(2-methylphenoxy)propyl]oxazole (6) 4-(4-chlorophenyl)-2-(2-methyl-1-imidazolyl)-5-[3-(3-methylphenoxy)propyl]oxazole (7) 5-[3-(4-chloro-2-methylphenoxy)propyl]-4-(4-chlorophenyl)-2-(2-methyl-1-imidazolyl)oxazole.

Hereinafter, these compounds are sometimes abbreviated simply as "compound (1)", "compound (2)", etc.

The salt of compound (I) is preferably a pharmacologically acceptable one. For example, a salt with an inorganic base, a salt with an organic base, a salt with an inorganic acid, a salt with an organic acid, a salt with a basic or acidic amino acid, and the like can be mentioned. Preferable examples of the salt with an inorganic base include alkali metal salts such as sodium salt, potassium salt etc.; alkaline earth metal salts such as calcium salt, magnesium salt; and aluminum salt, ammonium salt and the like.

Preferable examples of the salt with an organic base include salts with trimethylamine, triethylamine, pyridine, picoline, ethanolamine, diethanolamine, triethanolamine, dicyclohexylamine, N,N'-dibenzylethylenediamine, and the like.

Preferable examples of the salt with an inorganic acid include salts with hydrochloric acid, hydrobromic acid, nitric acid, sulfuric acid, phosphoric acid, and the like.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salt with a basic amino acid include salts with arginine, lysine and ornithine, and the like.

Preferable examples of the salt with an acidic amino acid include salts with aspartic acid, glutamic acid, and the like.

The compound (I) and a salt thereof can be produced by a method known per se. Examples of such method include the methods described in, for example, WO01/14372, JP-A-58-183676 (EP-A 92239), JP-A-59-190979, JP-A-09-323983 (WO97/36882), and the like, and modifications thereof, and the like.

The compound (I) and a salt thereof of the present invention may be in the form of a hydrate.

The compound (I) of the present invention may be used in the form of a prodrug. The prodrug of compound (I) as used herein means a compound capable of being converted to compound (I) or a salt thereof in vivo by the action of an enzyme, gastric juice and the like under physiological conditions, namely, a compound capable of being converted to compound (I) upon enzymatic oxidation, reduction, hydrolysis and the like, or a compound capable of being converted to compound (I) upon hydrolysis by gastric juice etc., and the like. The, prodrug of compound (I) includes compounds derived by acylation, alkylation or phosphorylation of the amino group of compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of compound (I), etc.), compounds derived by acylation, alkylation, phosphorylation or boration of the hydroxy group of compound (I) (e.g., compounds derived by acetylation, palmitoylation, propanoylation, pivaloylation, succinylation, fumarylation, alanylation or dimethylaminomethylcarbonylation of the hydroxy group of compound (I), etc.), and compounds derived by esterification or amidation of the carboxyl group of compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of compound (I), etc.), and the like. These compounds can be produced from compound (I) by methods known per se.

The prodrug of compound (I) may be one capable of being converted to compound (I) under physiological conditions, as described in "Iyakuhin no Kaihatsu (Development of Drugs)", vol 7, Molecular Designing, published by Hirokawa Shoten, 1990, pages 163-198.

The compound (I) may be labeled with an isotope (e.g., $^3H$, $^{14}C$, $^{35}S$, $^{125}I$, etc.), and the like The compound (I), a salt thereof and a prodrug thereof (hereinafter sometimes to be abbreviated simply as "compound of the present invention") are low in toxicity and can be safely administered to mammals (e.g., human, mouse, rat, rabbit, dog, cat, bovine, horse, swine, monkey etc.).

In the present invention, the TGF-β superfamily of the TGF-β superfamily production/secretion promoter means a protein group wherein the arrangement of cysteine in mature molecules has a characteristic structure, and is known to exhibit diverse actions on various cells and tissues. Specific examples thereof include TGF-β 1, TGF-β 2, TGF-β 3, BMP (osteogenic factor, bone morphogenetic protein)-2, BMP-3, BMP-4, BMP-5, BMP-6, BMP-7, BMP-8A, BMP-8B, BMP-14 (GDF-5), GDNF (glial cell line-derived neurotrophic factor), neurturin, artemin, persephin, GDF-1, GDF-8, GDF (growth/differentiation factor)-15, inhibin α, inhibin β, DAF (dauer formation) 7 and the like can be mentioned. As the TGF-β superfamily, GDNF, GDF-15 and the like-are preferable.

In addition, the TGF-β superfamily production/secretion promoter means a pharmaceutical agent which increases the amount of TGF-β superfamily in living organisms by activating the production and/or secretion capability of the TGF-β superfamily in living organisms and promoting the production and/or secretion of the TGF-β superfamily. For example, a pharmaceutical agent that causes production and/or secretion of the TGF-β superfamily in a living organism, even when TGF-β superfamily is void in the living organisms due to the abnormality in the production and/or secretory function of the TGF-β superfamily in the living organism, is also encompassed in the TGF-β superfamily production/secretion promoter of the present invention.

While the TGF-β superfamily production/secretion promoter of the present invention (hereinafter sometimes to be abbreviated as the agent of the present invention) can be the compound of the present invention itself, it is generally obtained by formulating a preparation according to a method known per se, using the compound of the present invention and a pharmacologically acceptable carrier.

As the pharmacologically acceptable carrier, those various organic or inorganic carrier substances, which are conventionally used as materials of pharmaceutical preparations, can be used. As concrete examples thereof, excipients, lubricants, binders, disintegrants or the like in solid preparations; solvents, solubilizers, suspending agents, isotonizing agents, buffers, soothing agents or the like in liquid preparations, and the like can be mentioned. In preparation, additives such as preservatives, antioxidants, coloring agents and sweeteners may be used as necessary.

Preferable examples of the excipients include lactose, saccharose, D-mannitol, D-sorbitol, starch, pre-gelatinized starch, dextrin, crystalline cellulose, low-substituted hydroxypropylcellulose, carboxymethylcellulose sodium, powdered acacia, pullulan, light silicic anhydride, synthetic aluminum silicate, magnesium aluminometasilicate, xylitol, sorbitol, erythritol and the like.

Preferable examples of the lubricants include magnesium stearate, calcium stearate, talc, colloidal silica, polyethylene glycol 6000, and the like.

Preferable examples of the binders include pre-gelatinized starch, sucrose, gelatin, powdered acacia, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferable examples of the disintegrants include lactose, saccharose, starch, carboxymethylcellulose, carboxymethylcellulose calcium, croscarmellose sodium, carboxymethylstarch sodium, low-substituted hydroxypropylcellulose, light silicic anhydride, calcium carbonate and the like.

Preferable examples of the solvents include water for injection, physiological saline, Ringer's solution, alcohol, propylene glycol, polyethylene glycol, sesame oil, corn oil, olive oil, cotton-seed oil, and the like.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agents include surfactants such as stearyl triethanolamine, sodium lauryl sulfate, laurylaminopropionic acid, lecithin, benzalkonium chloride, benzethonium chloride, glycerol monostearate and like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene-hardened castor oil, and the like.

Preferable examples of the isotonizing agents include sodium chloride, glycerol, D-mannitol, D-sorbitol, glucose, xylitol, fructose and the like.

Preferable examples of the buffers include buffer solutions of phosphate, acetate, carbonate, citrate and the like.

Preferable examples of the soothing agents include propylene glycol, lidocaine hydrochloride, benzyl alcohol and the like.

Preferable examples of the preservatives include para-hydroxybenzoate esters, chlorobutanol, benzyl alcohol; phenethyl alcohol, dehydroacetic acid, sorbic acid and the like.

Preferable examples of the antioxidants include sulfite salts, ascorbate salts and the like.

Preferable examples of the coloring agents include water-soluble colored tar dyes (e.g., food colors such as Food Color Red No. 2 and No. 3, Food Color Yellow No. 4 and No. 5, Food Color Blue No. 1 and No. 2), water-insoluble lake colors (e.g., the aluminum salt of the above water-soluble edible tar colors), and natural colors (e.g., β-carotene, chlorophyll, red iron oxide and the like), and the like.

Preferable examples of the sweeteners include saccharin sodium, dipotassium glycyrrhizinate, aspartame, stevia and the like.

As the dosage form of the agent of the present invention, for example, oral preparations such as tablets (including sublingual tablet and intraorally disintegrating tablet), capsules (including soft capsules and microcapsules), granules, powders, troches, syrups, emulsions, suspensions and the like; and parenteral preparations such as injections (e.g., subcutaneous injection, intravenous injection, intramuscular injection, intraperitoneal-injection and the like), drip infusions, external preparations (e.g., intranasal preparations, transdermal preparations, ointments and the like), suppositories (e.g., rectal suppositories, vaginal suppositories), pellets, solutions for instillation, eye drops, nasal drops, transpulmonary agents (inhalant) and the like can be mentioned.

These preparations may be controlled-release preparations (e.g., sustained-release microcapsules and the like), such as rapid release preparations, sustained-release preparations and the like.

These preparations can be produced according to methods well established in the fields of the pharmaceutical manufacturing techniques, for example, by the methods described in the Japanese Pharmacopoeia, and the like. In the following, some typical methods for producing various preparations are described in detail. The content of compound of the present invention in the agent of the present invention ranges, for instance, 0.1 to 100% by weight.

The production methods of the oral preparations and parenteral preparations are specifically explained in the following.

The oral preparations are produced by adding, to an active ingredient, for example, excipients (e.g., lactose, saccharose, starch, D-mannitol, xylitol, sorbitol, erythritol, crystalline cellulose, light silicic anhydride etc.), disintegrants (e.g., calcium carbonate, starch, carboxymethyl cellulose, carboxymethyl cellulose calcium, low-substituted hydroxypropylcellulose, crosscarmellose sodium, carboxymethyl starch sodium, light silicic anhydride etc.), binders (e.g., pre-gelatinized starch, powdered acacia, carboxymethylcellulose, hydroxypropylcellulose, hydroxypropylmethylcellulose, polyvinylpyrrolidone, crystalline cellulose, methylcellulose, saccharose, D-mannitol trehalose, dextrin etc.), lubricants (e.g., talc, magnesium stearate, calcium stearate, colloidal silica, polyethylene glycol 6000 etc.) and the like and compression molding the obtained mixture.

Further, with the aim of masking of taste, or imparting enteric or sustained-release property, the oral preparations may be coated by a method known per se. As the coating agent, for example, an enteric polymer (e.g., cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose etc.), gastric-soluble polymer (e.g., polyvinyl acetal diethylaminoacetate, aminoalkylmethacrylate copolymer E etc.), water-soluble polymer (e.g., hydroxypropylcellulose, hydroxypropylmethylcellulose etc.), water-insoluble polymer (e.g., ethylcellulose, aminoalkyl methacrylate copolymer RS, ethyl acrylate/methyl methacrylate copolymer etc.), wax and the like can be used. When coating is performed, plasticizers such as polyethylene glycol and the like, light shielding agents such as titanium oxide, ferric oxide and the like may be used together with the above-mentioned coating agent.

Injections are produced by dissolving, suspending or emulsifying the active ingredient in an aqueous solvent (e.g., distilled water, physiological saline, Ringer's solution etc.) or an oleaginous solvent (e.g., vegetable oils such as olive oil, sesame oil, cotton seed oil, corn oil etc.; propylene glycol, macrogol, tricapryline and the like), together with a dispersant (e.g., Tween 80 (Atlas Powder Company, USA), HCO 60 (Nikko Chemicals), polyethylene glycol, carboxymethylcellulose, sodium alginate etc.), a preservative (e.g., methylparaben, propylparaben, benzyl alcohol, chlorobutanol, phenol etc.), an isotonizing agent (e.g., sodium chloride, glycerol, D-sorbitol, D-mannitol, xylitol, glucose, fructose etc.) and the like.

Where desired, additives such as solubilizers (e.g., sodium salicylate, sodium acetate, polyethylene glycol, propylene glycol, D-mannitol, trehalose, benzyl benzoate, ethanol, trisaminomethane, cholesterol, triethanolamine, sodium carbonate, sodium citrate etc.), suspending agents (e.g., surfactants such as stearyl triethanolamine, sodium lauryl sulfate, laurylaminopropionic acid, lecithin, benzalkonium chloride, benzethonium chloride, glycerine monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose etc., and the like), buffering agents (e.g., buffers such as phosphate, acetate, carbonate, citrate etc., and the like), stabilizers (e.g., human serum albumin etc.), soothing agents (e.g., propylene glycol, lidocaine hydrochloride, benzyl alcohol etc.), preservatives (e.g., p-oxybenzoic acid esters, chlorobutanol, benzalkonium chloride, benzyl alcohol, phenethyl alcohol, dehydroacetic acid, sorbic acid etc.) and the like can be used.

The external preparations are produced by making the active ingredient into a solid, semi-solid or liquid composition. For example, the above-mentioned solid composition is produced by using the active ingredient as it is, or by adding excipients (e.g., lactose, D-mannitol, starch, crystalline cellulose, saccharose and the like), thickeners (e.g., natural gums, cellulose derivatives, acrylic acid polymers and the like) and the like thereto, and mixing and powdering them. The above-mentioned liquid composition is produced in almost the same manner as the case of the injections. The semi-solid composition is preferably a water-based or oil-based gel, or ointment. Additionally, each of these compositions can contain pH adjusting agents (e.g., phosphoric acid, citric acid, hydrochloric acid, sodium hydroxide and the like), preservatives (e.g., p-oxybenzoic acid esters, chlorobutanol, benzalkonium chloride, benzyl alcohol, phenethyl alcohol, dehydroacetic acid, sorbic acid and the like), and the like.

The suppositories can be produced by making the active ingredient into an oil-based or water-based solid, semi-solid or liquid composition. As the oil-based base used for the production of said composition, for example, higher fatty acid glycerides [e.g., cacao butter, Witepsols (Huels Aktiengesellschaft, Germany) and the like], intermediate fatty acid triglycerides [e.g., miglyols (Huels Aktiengesellschaft, Germany) and the like], vegetable oils (e.g., sesame oil, soy bean oil, cotton seed oil and the like), and the like can be mentioned. As the water-based base, for example, polyethylene glycols, propylene glycol and the like can be mentioned. Additionally, as the water-based gel base, for example, natural gums, cellulose derivatives, vinyl polymers, acrylic acid polymers and the like can be mentioned.

The dose of the agent of the present invention may vary depending on the administration subject, route of administration, clinical conditions and other factors. Generally, however, in the case of orally administrating the agent of the present invention to adults, the compound of the present invention, which is the active ingredient, is administered in a single dose of generally about 0.05 to 500 mg/kg body weight, preferably about 0.5 to 100 mg/kg body weight. This dose is desirably administered once to three times a day.

When the agent of the present invention is orally administered to an adult patient suffering from dysautonomia (e.g., diabetic autonomic neuropathy etc.), the compound of the invention, which is the active ingredient, is administered in a single dose of about generally 0.05 to 50 mg/kg body weight, preferably 0.2 to 4 mg/kg body weight. This dose is desirably administered once to three times a day.

The agent of the present invention shows production/secretion promoting action for a TGF-$\beta$ superfamily, especially GDNF and GDF-15.

The agent of the present invention has no side effect, and it can be used as an agent for the prophylaxis or treatment of dysautonomia (e.g., diabetic autonomic nueropathy, asymptomatic hypoglycemia, gastroparesis, neurogenic diarrhea and constipation, erectile dysfunction, orthostatic hypotension, arrhythmia, cardiac insufficiency, painless cardiac infarction, dyshidrosis, neurogenic bladder), bladder dysfunction (e.g., bladder reflex disorder and the like), hearing impairment, diabetic foot, bone diseases (e.g., osteoporosis and the like), joint diseases (e.g., Charcot joint, osteoarthritis, rheumatism and the like), Hirschsprung's disease, epilepsia and the like; a promoter of cure of skin injury caused by metabolic or endocrine system diseases such as diabetes and the like, and by wound; a pancreatic regeneration agent (pancreatic function restoring agent); a renal regeneration agent (renal function restoring agent); a pain suppressing agent; a prophylactic agent of amputation of lower limb; an agent for the prophylaxis of sudden death; and the like.

Also, the agent of the present invention can be used as an agent for the prophylaxis or treatment of schizophrenia, drug dependence, peripheral neuropathy (e.g., diabetic neuropathy, cancer treatment-induced neuropathy and the like), diabetic cardiac myopathy, peripheral nerve injury, spinal injury, amyotrophic lateral sclerosis (ALS), multiple sclerosis, cerebral ischemic disease, Alzheimer type senile dementia, Parkinson's disease, Huntington's chorea, depression, inflammatory bowel disease, chronic pain (e.g., cancer pain and the like), problematic behavior associated with dementia (e.g., wandering, aggressive behavior and the like), anxiety, numbness and pain by wound, and the like; as well as an ameliorating agent of peripheral neuropathy or brain metabolic disorder.

In addition, the agent of the present invention can be also used as an agent for the prophylaxis or treatment of diseases such as diabetes (e.g., type I diabetes, type II diabetes, gestational diabetes etc.), impaired glucose tolerance, hyperlipidemia (e.g., hypertriglyceridemia, hypercholesterolemia, hypo-HDL-emia, postprandial hyperlipidemia, etc.), hyperinsulinemia, obesity, hyperphagia, hypertension, cardiovascular diseases (e.g., atherosclerosis, etc.); or syndromes (e.g., syndrome X, visceral obesity syndrome, etc.) having some of these diseases in combination.

Furthermore, the agent of the present invention can be used for the secondary prophylaxis and the suppression of development of the above-mentioned various diseases or abnormalities.

The agent of the present invention can be used in combination with a drug such as a therapeutic agent of diabetes, a therapeutic agent for diabetic complications, an antihyperlipemic agent, an antihypertensive agent, an antiobesity agent, a diuretic, a chemotherapeutic agent, an immunotherapeutic agent, an agent for ameliorating cachexia, an agent acting on peripheral and central nerves, a therapeutic agent for ulcers, an anti-inflammatory agent, and the like (hereinafter sometimes referred to briefly as combination drug). On such occasions, the time of administration of the agent of the present invention and that of the combination drug are not limited, and they may be administered simultaneously or at staggered times to the administration subject.

Said combination drug may be a low molecular weight compound, and may also be a high molecular weight protein, polypeptide, antibody or vaccine and the like. The dose of the combination drug can be appropriately selected based on the dose clinically employed. The proportion of the agent of the present invention and the combination drug can be appropriately selected according to the administration subject, administration route, target disease, clinical condition, combination, and the like. When the administration subject is human, for example, the combination drug may be used in an amount of 0.01 to 100 parts by weight per part by weight of the agent of the present invention.

Examples of the therapeutic agent of diabetes include insulin preparations (e.g., animal insulin preparations obtained by extraction from the bovine or swine pancreas; human insulin preparations synthesized by a genetic engineering technique using *Escherichia coli* or a yeast; insulin-zinc; protamine-insulin-zinc, a fragment or derivative of insulin (e.g., INS-1 etc.)), insulin sensitizers (e.g., pioglitazone hydrochloride, troglitazone, rosiglitazone or its maleate, JTT-501, MCC-555, YM-440, GI-262570, KRP-297, FK-614, CS-011, compounds described in WO99/58510 (e.g., (E)-4-[4-(5-methyl-2-phenyl-4-oxazolylmethoxy)benzyloxyimino]-4-phenylbutyric acid), NN-622, AZ-242, BMS-298585, ONO-5816, LM-4156, BM-13-1258, MBX-102, GW-1536 etc.), α-glucosidase inhibitors (e.g., voglibose, acarbose, miglitol, emiglitate etc.), biguanides (e.g., phenformin, metformin, buformin etc.), sulfonylureas (e.g., tolbutamide, glibenclamide, gliclazide, chlorpropamide, tolazamide, acetohexamide, glyclopyramide, glimepiride etc.), and other insulin secretagogues (e.g., repaglinide, senaglinide, mitiglinide or its calcium salt hydrate, GLP-1, nateglinide etc.), dipeptidylpeptidase IV inhibitors (e.g., NVP-DPP-278, PT-100, P32/98, NVP-DPP-728, LAF-237 etc.), β3 agonists (e.g., CL-316243, SR-58611-A, UL-TG-307, AJ-9677, AZ40140 etc.), amyrin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.), and the like.

Examples of the therapeutic agent for diabetic complications include aldose reductase inhibitors (e.g., tolrestat, epalrestat, zenarestat, zopolrestat, fidarestat (SNK-860), minalrestat (ARI-509), CT-112 etc.), neurotrophic factors (e.g., NGF, NT-3 etc.), AGE inhibitors (e.g., ALT-945, pimagedine, pyratoxathine, N-phenacylthiazolinium bromide (ALT-766), EXO-226 etc.), active oxygen scavengers (e.g., thioctic acid etc.), cerebral vasodilators (e.g., tiopuride etc.), and the like.

Examples of the antihyperlipemic agent include statin compounds which are cholesterol synthesis inhibitors (e.g., pravastatin, simvastatin, lovastatin, atorvastatin, fluvastatin, cerivastatin and salts thereof (e.g., sodium salt etc.) and the like), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate, beclofibrate, binifibrate, ciprofibrate, clofibric acid, etofibrate, fenofibrate, gemfibrozil, nicofibrate, pirifibrate, ronifibrate, theofibrate and the like), ACAT inhibitors (e.g., avasimibe, eflucimibe and the like), anion exchange resins (e.g., colestyramine and the like), probucol, nicotinic acid drugs (e.g., nicomol, niceritrol and the like), ethyl icosapentate, plant sterols (e.g., soysterol, γ-oryzanol and the like) and the like.

Examples of the antihypertensive agent include angiotensin converting enzyme inhibitors (e.g., captopril, enalapril, delapril etc.), angiotensin II antagonists (e.g., losartan, candesartan cilexetil etc.), calcium antagonists (e.g., manidipine, nifedipine, amlodipine, efonidipine, nicardipine etc.), potassium channel openers (e.g., levcromakalim, L-27152, AL 0671, NLP-121 etc.), clonidine, and the like.

Examples of the antiobesity agent include antiobesity drugs acting on the central nervous system (e.g., dexfenfluramine, fenfluramine, phentermine, sibutramine, anfepramon, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, AJ-9677, AZ40140 etc.), anorectic peptides (e.g., leptin, CNTF (ciliary neurotrophic factor)), cholecystokinin agonists (e.g., lintitript, FPL-15849 etc.), and the like.

Examples of the diuretic include xanthine derivatives (e.g., theobromine and sodium salicylate, theobromine and calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydrogenase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide, etc.

Examples of the chemotherapeutic agent include alkylating agents (e.g., cyclophosphamide, ifosamide etc.), metabolic antagonists (e.g., methotrexate, 5-fluorouracil and its derivative etc.), antitumor antibiotics (e.g., mitomycin, adriamycin etc.), plant-derived antitumor agents (e.g., vincristine, vindesine, Taxol etc.), cisplatin, carboplatin, etoposide, and the like. Of these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating agents (e.g., granulocyte colony stimulating factor, erythropoietin etc.), and the like. Of these, interleukins such as IL-1, IL-2, IL-12 and the like are preferable.

As the agent for ameliorating cachexia, for example, cyclooxygenase inhibitors (e.g., indomethacin etc.) (*Cancer Research*, vol. 49, pp. 5935-5939, 1989), progesterone derivatives (e.g., megestrol acetate) (*Journal of Clinical Oncology*, vol. 12, pp. 213-225, 1994), glucocorticoids (e.g., dexamethasone etc.), metoclopramide pharmaceuticals, tetrahydrocannabinol pharmaceuticals (the above references are applied to both), fat metabolism ameliorating agents (e.g., eicosapentanoic acid etc.) (*British Journal of Cancer*, vol. 68, pp. 314-318, 1993), growth hormones, IGF-1, and antibodies to the cachexia-inducing factor TNF-$\alpha$, LIF, IL-6 or oncostatin M, and the like can be mentioned.

As the agent acting on peripheral and central nerves, for example, acetylcholine esterase inhibitors (e.g., tacrine, donepezil, rivastigmin, galanthamine etc.), dopamine receptor agonists (e.g., L-dopa, apomorphine and the like), monoamine intake inhibitors (e.g., tramadol), GABA receptor agonists (e.g., Gabapentin), acetylcholine receptor ligands (e.g., ABT-594) and the like can be mentioned.

As the therapeutic agent for ulcers, for example, therapeutic agents of skin ulcer, such as Prostaglandin preparations (e.g., Prostaglandin E1), growth factor preparations (e.g., PDGF), and the like can be mentioned.

As the anti-inflammatory agent, for example, antirheumatic agents (e.g., leflunomide), and the like can be mentioned.

Further, glycation inhibitors (e.g., ALT-711), nerve regeneration stimulators (e.g., Y-128, VX853, prosaptide etc.), antidepressants (e.g., desipramine, amitriptyline, imipramine), anticonvulsant (e.g., lamotrigine), antiarrhythmics (e.g., mexiletine), endothelin receptor antagonists (e.g., ABT-627), narcotic analgesics (e.g., morphine), $\alpha 2$ receptor agonists (e.g., clonidine), focal analgesics (e.g., capsaicin), protein kinase C inhibitors (e.g., LY-333531), anxiolytics (e.g., benzodiazepin), phosphodiesterase inhibitors (e.g., sildenafil), therapeutic agents of osteoporosis (e.g., alfacalcidol, carcitriol, elcatonin, calcitonin salmon, estriol, ipriflavone, pamidronate disodium, alendronate sodium hydrate, incadronate disodium etc.), therapeutic agents of incontinentia or pollakiuria (e.g., flavoxate hydrochloride, oxybutynin hydrochloride, propiverine hydrochloride etc.) and the like can be also used in combination with the agent of the present invention.

Use of the agent of the present invention in combination with the above combination drug provides excellent effects such as effects of enhancing the action of the agent of the present invention and/or the combination drug, effects of reducing the dose of the agent of the present invention and/or the combination drug, effects of reducing the side effects of the agent of the present invention and/or the combination drug, etc.

The present invention further relates to an agent for neuroneogenesis comprising compound (I), a salt thereof or a prodrug thereof.

Here, the agent for neuroneogenesis means a pharmaceutical agent which differentiates neuronal precursor cells (e.g., stem cells and the like) into nerve cells. Furthermore, the agent for neuroneogenesis may be a pharmaceutical agent which promotes differentiation of neuronal precursor cells into nerve cells.

The agent for neuroneogenesis of the present invention has low toxicity, and it can be administrated to mammals (e.g., human, mouse, rat, rabbit, dog, cat, bovine, horse, pig, monkey etc.) safely. Said agent for neuroneogenesis is useful as a prophylactic or therapeutic agent for, for example, motor function disorders caused after affection with various diseases (e.g., diabetes), fracture, a traffic accident and the like; cardiac function disorders or cerebral function attrition caused after a cardiovascular accident or a cerebral blood vessel accident, furthermore it is effective for accelerating the curing of these motor function disorders, cardiac function disorders or cerebral function attrition and the like.

The agent for neuroneogenesis of the present invention can be prepared in the same manner as the aforementioned TGF-$\beta$ superfamily production/secretion promoter. The dosage form, dose and the like of the agent for neuroneogenesis are the same as in the case of the TGF-$\beta$ superfamily production/secretion promoter. Also, said agent for neuroneogenesis can be used in combination with the aforementioned various combination drugs.

Furthermore, the present invention relates to an agent for restoring nerve function, which comprises a TGF-$\beta$ superfamily production/secretion promoter.

Here, the agent for restoring nerve function means a pharmaceutical agent having the activity of bringing the nerve function (e.g., secretion of neurotransmitter, and the like), which has become abnormal due to the application of various kinds of damages such as a stress load and the like, to the right direction.

In this specification, the TGF-$\beta$ superfamily production/secretion promoter is not particularly limited as long as it is a pharmaceutical agent having a TGF-$\beta$ superfamily production/secretion promoting activity. Here, as the TGF-$\beta$ superfamily, the aforementioned superfamily can be mentioned. The TGF-$\beta$ superfamily production/secretion promoter means a pharmaceutical agent which increases the amount of TGF-$\beta$ superfamily in living organisms by activating the production and/or secretion capability of TGF-$\beta$ superfamily in living organisms and promoting the production and/or secretion of TGF-$\beta$ superfamily. For example, a pharmaceutical agent that causes production and/or secretion of TGF-$\beta$ superfamily in living organisms, even when TGF-$\beta$ superfamily is void in living organism due to the abnormality in the production and/or secretory function of TGF-$\beta$ superfamily in the living organism, is also encompassed in the TGF-$\beta$ superfamily production/secretion promoter.

Specific examples of the TGF-$\beta$ superfamily production/secretion promoter include the aforementioned compound of the present invention, db-cAMP (dibutyl-cyclic adenosine monophosphate), PDD (phorbol 12,13-didecanoate), PGE2 (prostaglandin E2) and the like. Of these, the compound of the present invention is preferable.

The agent for restoring nerve function of the present invention has low toxicity, and can be administrated safely to mammals (e.g., human, mouse, rat, rabbit, dog, cat, bovine, horse, pig, monkey etc.). Said agent for restoring nerve function is useful as a prophylactic or therapeutic agent for, for example, motor function disorders caused after affection with various diseases (e.g., diabetes), fracture, a traffic accident and the like; cardiac function disorders or cerebral function attrition caused after a cardiovascular accident or a cerebral blood vessel accident, furthermore, it is effective for the accelerating the curing of these motor function disorders, cardiac function disorders or cerebral function attrition and the like.

The agent for restoring nerve function of the present invention can be prepared in the same manner as the aforementioned TGF-β superfamily production/secretion promoter. The dosage form, dose and the like of the agent for restoring nerve function are the same as in the case of the TGF-β superfamily production/secretion promoter. Also, said agent for restoring nerve function can be used in combination with the aforementioned various combination drugs.

The present invention further relates to an agent for the prophylaxis or treatment of dysautonomia, which comprises a TGF-β superfamily production/secretion promoter.

In this specification, the dysautonomia means a state where a nerve control system that maintains homeostasis of various living organisms, such as respiration, blood pressure, cardiac beat, sleep, excretion, food intake, internal secretion and the like, cannot show its normal function. As specific examples thereof, diabetic autonomic neuropathy, asymptomatic hypoglycemia, gastroparesis, neurogenic diarrhea and constipation, erectile dysfunction, orthostatic hypotension, arrhythmia, cardiac insufficiency, painless cardiac infarction, dyshidrosis, neurogenic bladder and the like can be mentioned.

The agent for the prophylaxis or treatment of dysautonomia of the present invention has low toxicity, and can be administrated safely to mammal (e.g., human, mouse, rat, rabbit, dog, cat, bovine, horse, pig, monkey etc.).

The agent for the prophylaxis or treatment of dysautonomia of the present invention can be prepared in the same manner as the aforementioned TGF-β superfamily production/secretion promoter. The dosage form, dose and the like of the agent for the prophylaxis or treatment of dysautonomia are the same as in the case of the TGF-β super family production/secretion promoter. In addition, this agent for the prophylaxis or treatment can be used in combination with the aforementioned various combination drugs.

The present invention further relates to an agent for the prophylaxis or treatment of bladder dysfunction, which comprises a TGF-β superfamily production/secretion promoter.

In this specification, the bladder dysfunction means a state where the function necessary for storing and excreting urine, i.e., bladder reflex and muscularis of urinary bladder does not function normally, and as specific examples, bladder reflex disorder, neurogenic bladder, disappearance of uroschesis, abnormal residual urine, atonic bladder and the like can be mentioned.

The agent for the prophylaxis or treatment of bladder dysfunction of the present invention has low toxicity and can be administrated safely to mammals (e.g., human, mouse, rat, rabbit, dog, cat, bovine, horse, pig, monkey etc.).

The agent for the prophylaxis or treatment of bladder dysfunction of the present invention can be prepared in the same manner as in the aforementioned TGF-β superfamily production/secretion promoter. The dosage form, dose and the like of the agent for the prophylaxis or treatment of bladder dysfunction are the same as in the case of the TGF-β super family production/secretion promoter. In addition, this agent for the prophylaxis or treatment can be used in combination with the aforementioned various combination drugs.

The following Examples and Experimental Examples are intended to describe the present invention in further detail and should by no means be construed as defining the scope of the invention. Unless mentioned otherwise, % means percent by weight.

In this specification, when base, amino acid and the like are expressed in abbreviation, they are based on abbreviation by IUPAC-IUB Commision on Biochemical Nomenclature or conventional abbreviation in this field.

The sequence numbers in the sequence listing in the present specification show the following sequences.

[SEQ ID:1]

The base sequence of primer used in Experimental Example 2.

[SEQ ID:2]

The base sequence of primer used in Experimental Example 2.

[SEQ ID:3]

The base sequence of probe used in Experimental Example 2.

EXAMPLES

Example 1

Production of Capsules

| | |
|---|---|
| 1) Compound (1) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

Example 2

Production of Tablets

| | |
|---|---|
| 1) Compound (1) | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound (1).

Example 3

Production of Capsules

| | |
|---|---|
| 1) Compound (5) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

Example 4

Production of Tablets

| | |
|---|---|
| 1) Compound (5) | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound (5).

Example 5

Production of Film-Coated Tablets

[Production of a Coating Agent]

209.6 g of hydroxypropylmethylcellulose 2910 (TC-5) and 42.0 g of Macrogol 6000 (polyethylene glycol 6000) were dissolved in 2520 g of purified water. In the solution thus obtained, 28.0 g of titanium oxide and 0.4 g of yellow ferric oxide were dispersed to give a coating agent.

[Production of Plain Tablets]

In a fluidized-bed granulating dryer (FD-3S, POWREX), 62.5 g of Compound (5), 3738 g of lactose and 750.0 g of corn starch were mixed uniformly. In the dryer, granulation was carried out while spraying an aqueous solution in which 150 g of hydroxypropylcellulose (HPC-L) was dissolved. Then, drying was carried out in the fluidized-bed granulating dryer.

The obtained granules were crushed by a Power-Mill pulverizer (P-3, Showa Machinery Co., Ltd.) with a punching screen of 1.5 mm to give pulverized powders.

To 4136 g of the pulverized powders, 220 g of croscarmellose sodium and 44 g of magnesium stearate were added, which was mixed in a tumble mixer (TM-15, Showa Machinery Co., Ltd.) to yield granules for tableting. Plain tablets were obtained by tableting the obtained granules with a rotary tableting machine (Correct 19K, Kikusui Seisakusho Co., Ltd.) with a punch of 8.5 mm$\phi$ at the weight of 200 mg (tableting pressure: 7 KN/punch).

[Production of Film-Coated Tablets]

The above coating agent was sprayed onto the obtained plain tablets in a Driacoater coating machine (DRC-500, POWREX) to yield 19000 film-coated tablets having the following prescription and containing 2.5 mg of Compound (5) per tablet.

| | (Composition per tablet) |
|---|---|
| Prescription of plain tablets | |
| 1) Compound (5) | 2.5 mg |
| 2) Lactose | 149.5 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |
| Prescription of film-coated tablets | |
| 1) Plain tablet | 200.0 mg |
| (Film ingredients) | |
| 2) Hydroxymethylcellulose2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

Example 6

Production of Film-Coated Tablets 19000 film-coated tablets, having the following prescription and containing 15 mg of Compound (5) per tablet, were produced in the same manner as in Example 5 except that the amount of Compound (5) and lactose used was 375.0 g and 3425 g, respectively.

| | (Composition per tablet) |
|---|---|
| Prescription of plain tablets | |
| 1) Compound (5) | 15.0 mg |
| 2) Lactose | 137.0 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |
| Prescription of film-coated tablets | |
| 1) Plain tablet | 200.0 mg |
| (Film ingredients) | |
| 2) Hydroxymethylcellulose 2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

Example 7

Production of Film-Coated Tablets 19000 film-coated tablets, having the following prescription and containing 60 mg of Compound (5) per tablet, were produced in the same manner as in Example 5 except that the amount of Compound (5) and lactose used was 1500.0 g and 2300 g, respectively.

|  | (Composition per tablet) |
| --- | --- |
| Prescription of plain tablets | |
| 1) Compound (5) | 60.0 mg |
| 2) Lactose | 92.0 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |
| Prescription of film-coated tablets | |
| 1) Plain tablet | 200.0 mg |
| (Film ingredients) | |
| 2) Hydroxymethylcellulose 2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

Experimental Example 1

17 week-old female KKAy mice (n=10-12) were maintained for 7 weeks on a powder feed (CRF-1, manufactured by Oriental Yeast Co., Ltd.) containing 0.01% of compound (5). Then, sciatic nerve of the mouse was taken and stored at −80° C., until use for the measurement (ca. 10 months).

The stored sciatic nerve was ultrasonicated in a 20-fold volume of a homogenized buffer (0.1 M tris hydrochloride buffer containing 1M sodium chloride, 2% BSA, 2 mM EDTA, 80 trypsin unit/L of aprotinin, 0.02% sodium azide, pH 7.6) and insoluble materials were separated by centrifugation (15,000 rpm, 30 min). The GDNF content of the supernatant was measured by the following ELISA method.

Thus, an anti-hGDNF goat antibody (100 µg/ml) (Genzyme-Techne) was distributed in 10-µl portions in the wells of 96-well round bottom plates and antibody adsorption was allowed to proceed by 2 hours incubation at room temperature. After removing the antibody, each well was washed three times with a washing solution. A 10-µl portion of the above supernatant or standard hGDNF (Oncogene Corporation) solution was placed in each well and the plates were incubated at room temperature for 2.5 hrs. After three times washings of each well, 20 µl of biotinylated anti-hGDNF goat antibody (Genzyme-Techne) (35 ng/ml) was added thereto, followed by overnight incubation at 4° C. After washing the biotinylated anti-hGDNF goat antibody, 20 µl of β-D-galactosidase-labeled streptoavidin (produced by Boehringer Mannheim) was added, and the mixture was incubated at room temperature for 1 hr. After washing, 30 µl of 4-methylumbelliferyl-β-D-galactoside (produced by Sigma) (10 µg/ml) was added to the substrate, the reaction was allowed to proceed at room temperature for 4 hours and then terminated by addition of 130 µl of 0.1 M glycine-sodium hydroxide buffer (pH 10.3), and the fluorescent intensity of the 4-methylumbelliferone produced was determined (Ex: 360 nm; Em: 450 nm). The amount of hGDNF in the compound (5) administration group was calculated based on a standard curve and determined in terms of relative multiplicity in relation to the amount of hGDNF in the compound (5) non-administration group (control).

As a result, the GDNF content of compound (5) administration group in the sciatic nerve increased by 87.9% as compared to the control group.

Experimental Example 2

Streptozotocin (STZ) was administered to 6-week-old male SD rats (n=5-8) at 70 mg/kg to prepare diabetic neuropathy models. Starting from 4 months of the STZ administration, compound (5) was orally administered to the rats for 4 months at the dose of 10 mg/kg body weight/day. Then, dorsal root ganglion of the rats was removed, treated with ISOGEN solution (NIPPON GENE CO., LTD.) and the total RNA was extracted.

Using the obtained total RNA, a primer depicted in 5'-ACTGCATGCCAACCAGAGC-3' (SEQ ID:1) and a primer depicted in 5'-TCGCACCTCTGGACTGAGTATC-3' (SEQ ID:2), which were prepared based on the reported mRNA sequence of GDF-15, and a fluorescent probe having a GDF-15 specific sequence, ACTCAGAACCAACCCCTGAC-CCAGC (SEQ ID:3), and acidic ribosomal phosphoprotein PO as an endogenous control, a real time quantitative RT-PCR (Applied Biosystems) was performed. As a result, GDF-15 expression level of the compound (5) administration group increased by 135% as compared to that of compound (5) non-administration group (control group).

Experimental Example 3

Streptozotocin (STZ, 70 mg/kg) was intravenously injected to 6-week-old male SD rats (n=9-10) to prepare diabetic neuropathy models. After 2 weeks of the STZ administration, the left sciatic nerve of the rats was transected under anesthesia, and compound (5) was orally administered at the dose of 10 mg/kg body weight/day for 5 weeks.

After the completion of the administration, the rats were anesthetized, and the distance (maximum distance of extension) from the nerve transection site to the detectable site was measured for evoked potential using a device detecting evoked potential [Neuropack 2, manufactured by NIHON KOHDEN CORPORATION]. As a result, the maximum extension of the compound (5) administration group was extended by 2.4 times as compared to that of the compound (5) non-administration group (control group).

To conclude, an effect of neuroneogenesis and an effect of restoring nerve function were observed in the compound (5) administration group:

INDUSTRIAL APPLICABILITY

The TGF-β superfamily production/secretion promoter of the present invention has no side effect and can be used as an agent for the prophylaxis or treatment for dysautonomia (e.g., diabetic autonomic neuropathy, asymptomatic hypoglycemia, gastroparesis, neurogenic diarrhea and constipation, erectile dysfunction, orthostatic hypotension, arrhythmia, cardiac insufficiency, painless cardiac infarction, dyshidrosis, neurogenic bladder), bladder dysfunction (e.g., bladder reflex disorder and the like), hearing impairment, diabetic foot, bone diseases (e.g., osteoporosis and the like), joint diseases (e.g., Charcot's joint, osteoarthritis, rheumatism and the like), Hirschsprung's disease, epilepsia and the like; a promoter of cure of skin injury caused by metabolic or endocrine system diseases such as diabetes and the like, and by wound; a pancreatic regeneration agent (pancreatic function restoring agent); a renal regeneration agent (renal function restoring agent); a pain suppressing agent; a prophylactic agent of amputation of lower limb; an agent for the prophylaxis of sudden death; and the like.

optionally substituted thiol group or an optionally substituted amino group;

A is an optionally substituted formyl group, an optionally substituted $C_{1-10}$ alkyl-carbonyl group, an optionally substituted $C_{3-10}$ cycloalkyl-carbonyl group, an optionally substituted $C_{2-10}$ alkenyl-carbonyl group, an optionally substituted $C_{3-10}$ cycloalkenyl-carbonyl group, an optionally substituted $C_{6-12}$ aryl-carbonyl group, an optionally substituted phosphono group, an optionally substituted heterocyclic group, an optionally substituted hydroxy group or an optionally esterified carboxyl group;

The invention claimed is:

1. A method for promoting the production and/or secretion of a TGF-β superfamily protein in a mammal, which comprises administering a compound represented by the formula:

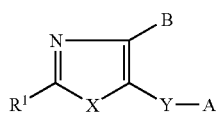

wherein

R¹ is a halogen atom, an optionally substituted heterocyclic group, an optionally substituted hydroxy group, an optionally substituted thiol group or an optionally substituted amino group;

B is an optionally substituted aromatic group;

X is an oxygen atom; and

Y is a divalent hydrocarbon group or heterocyclic group, or a salt thereof to the mammal.

2. A method for inducing neuroneogenesis in a mammal, which comprises administering a TGF-β superfamily protein production and/or secretion promoter to the mammal, wherein the TGF-β superfamily protein production and/or secretion promoter is a compound represented by the formula:

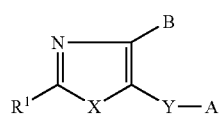

wherein
R¹ is a halogen atom, an optionally substituted heterocyclic group, an optionally substituted hydroxy group, an optionally substituted thiol group or an optionally substituted amino group;
A is an optionally substituted formyl group, an optionally substituted $C_{1-10}$ alkyl-carbonyl group, an optionally substituted $C_{3-10}$ cycloalkyl-carbonyl group, an optionally substituted $C_{2-10}$ alkenyl-carbonyl group, an optionally substituted $C_{3-10}$ cycloalkenyl-carbonyl group, an optionally substituted $C_{6-12}$ aryl-carbonyl group, an optionally substituted phosphono group, an optionally substituted heterocyclic group, an optionally substituted hydroxy group or an optionally esterified carboxyl group;
B is an optionally substituted aromatic group;
X is an oxygen atom; and
Y is a divalent hydrocarbon group or heterocyclic group, or a salt thereof.

3. A method for restoring nerve function in a mammal, which comprises administering a TGF-β superfamily protein production and/or secretion promoter to the mammal wherein the TGF-β superfamily protein production and/or secretion promoter is a compound represented by the formula:

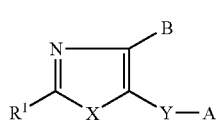

(I)

wherein
R¹ is a halogen atom, an optionally substituted heterocyclic group, an optionally substituted hydroxy group, an optionally substituted thiol group or an optionally substituted amino group;
A is an optionally substituted formyl group, an optionally substituted $C_{1-10}$ alkyl-carbonyl group, an optionally substituted $C_{3-10}$ cycloalkyl-carbonyl group, an optionally substituted $C_{2-10}$ alkenyl-carbonyl group, an optionally substituted $C_{3-10}$ cycloalkenyl-carbonyl group, an optionally substituted $C_{6-12}$ aryl-carbonyl group, an optionally substituted phosphono group, an optionally substituted heterocyclic group, an optionally substituted hydroxy group or an optionally esterified carboxyl group;
B is an optionally substituted aromatic group;
X is an oxygen atom; and
Y is a divalent hydrocarbon group or heterocyclic group, or a salt thereof.

4. A method for treating dysautonomia in a mammal, which comprises administering a TGF-β superfamily protein production and/or secretion promoter to the mammal wherein the TGF-β superfamily protein production and/or secretion promoter is a compound represented by the formula:

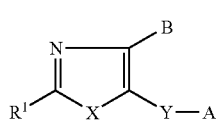

(I)

wherein
R¹ is a halogen atom, an optionally substituted heterocyclic group, an optionally substituted hydroxy group, an optionally substituted thiol group or an optionally substituted amino group;
A is an optionally substituted formyl group, an optionally substituted $C_{1-10}$ alkyl-carbonyl group, an optionally substituted $C_{3-10}$ cycloalkyl-carbonyl group, an optionally substituted $C_{2-10}$ alkenyl-carbonyl group, an optionally substituted $C_{3-10}$ cycloalkenyl-carbonyl group, an optionally substituted $C_{6-12}$ aryl-carbonyl group, an optionally substituted phosphono group, an optionally substituted heterocyclic group, an optionally substituted hydroxy group or an optionally esterified carboxyl group;
B is an optionally substituted aromatic group;
X is an oxygen atom; and
Y is a divalent hydrocarbon group or heterocyclic group, or a salt thereof.

5. A method for treating bladder dysfunction in a mammal, which comprises administering a TGF-β superfamily protein production and/or secretion promoter to the mammal, wherein the TGF-β superfamily protein production and/or secretion promoter is a compound represented by the formula:

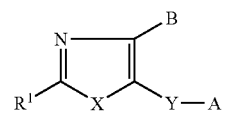

(I)

wherein
R¹ is a halogen atom, an optionally substituted heterocyclic group, an optionally substituted hydroxy group, an optionally substituted thiol group or an optionally substituted amino group;
A is an optionally substituted formyl group, an optionally substituted $C_{1-10}$ alkyl-carbonyl group, an optionally substituted $C_{3-10}$ cycloalkyl-carbonyl group, an optionally substituted $C_{2-10}$ alkenyl-carbonyl group, an optionally substituted $C_{3-10}$ cycloalkenyl-carbonyl group, an optionally substituted $C_{6-12}$ aryl-carbonyl group, an optionally substituted phosphono group, an optionally substituted heterocyclic group, an optionally substituted hydroxy group or an optionally esterified carboxyl group;
B is an optionally substituted aromatic group;
X is an oxygen atom; and
Y is a divalent hydrocarbon group or heterocyclic group, or a salt thereof.

6. The method of claim 1, wherein R¹ is an optionally substituted heterocyclic group.

7. The method of claim 1, wherein R¹ is an optionally substituted 5-membered nitrogen-containing aromatic heterocyclic group.

8. The method of claim 1, wherein R¹ is an optionally substituted imidazolyl group.

9. The method of claim 1, wherein A is an optionally substituted hydroxy group.

10. The method of claim 1, wherein A is an optionally substituted aryloxy group.

11. The method of claim 1, wherein A is a phenoxy group substituted by an optionally substituted alkyl group.

12. The method of claim 1, wherein B is an optionally substituted phenyl group.

13. The method of claim 1, wherein Y is a divalent aliphatic hydrocarbon group.

14. The method of claim 1, wherein the compound is 4-(4-chlorophenyl)-2-(2-methyl-1-imidazolyl)-5-[3-(2-methylphenoxy)propyl]oxazole.

15. The method of claim 1, wherein the TGF-β superfamily protein is GDNF.

16. The method of claim 1, wherein the TGF-β superfamily protein is GDF-15.

* * * * *